US012409329B2

(12) United States Patent
Rock et al.

(10) Patent No.: US 12,409,329 B2
(45) Date of Patent: Sep. 9, 2025

(54) METHOD AND APPARATUS FOR IMPLANTING A MEDICAL DEVICE IN A CORONARY SINUS

(71) Applicant: Medtronic, Inc., Minneapolis, MN (US)

(72) Inventors: Kaileigh E. Rock, Mahtomedi, MN (US); Ronald A. Drake, St. Louis Park, MN (US); Kathryn E. Hilpisch, Cottage Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 559 days.

(21) Appl. No.: 17/813,184

(22) Filed: Jul. 18, 2022

(65) Prior Publication Data

US 2023/0098146 A1   Mar. 30, 2023

Related U.S. Application Data

(60) Provisional application No. 63/250,431, filed on Sep. 30, 2021.

(51) Int. Cl.
*A61N 1/375* (2006.01)
*A61N 1/372* (2006.01)

(52) U.S. Cl.
CPC ..... *A61N 1/37518* (2017.08); *A61N 1/37205* (2013.01); *A61N 1/37512* (2017.08); *A61N 1/37516* (2017.08); *A61N 1/3756* (2013.01)

(58) Field of Classification Search
CPC ............ A61N 1/37518; A61N 1/37205; A61N 1/37512; A61N 1/37516; A61N 1/3756
See application file for complete search history.

(56) References Cited

U.S. PATENT DOCUMENTS

| 8,398,610 B2 * | 3/2013 | Locsin .............. A61M 25/0069 604/509 |
| 10,350,416 B2 | 7/2019 | Bonner et al. |
| 10,549,092 B1 * | 2/2020 | Hakki ..................... A61N 7/00 |

(Continued)

FOREIGN PATENT DOCUMENTS

WO   2021030392 A1   2/2021

OTHER PUBLICATIONS

Sanchez-Quintana et al., "Anatomical Basis for the Cardiac Interventional Electrophysiologist," Hindawi Publishing, BioMed Research International, vol. 2015, Article ID 547364, http://dx.doi.org/10.1155/2015/547364, Sep. 28, 2015, 25 pp.

(Continued)

*Primary Examiner* — Catherine M Voorhees
(74) *Attorney, Agent, or Firm* — Shumaker & Sieffert, P.A.

(57) ABSTRACT

A system for delivery of a leadless pacemaker. The system includes a catheter with an elongate flexible tubular body with a proximal end and a distal end, wherein the distal end of the tubular body includes a delivery cup with an external surface having an inflatable compliant balloon; and a pacing capsule of the leadless pacemaker releasably retained in the delivery cup. The pacing capsule includes an arrangement of tines configured to deploy and pierce a target tissue at a desired pacing capsule implant site in a coronary sinus of a patient. The balloon, when at least partially inflated, is configured to urge the delivery cup against the target tissue during deployment of the pacing capsule.

27 Claims, 12 Drawing Sheets

(56) References Cited

U.S. PATENT DOCUMENTS

| | | | |
|---|---|---|---|
| 10,653,859 B2 | 5/2020 | Eidenschink et al. | |
| 10,806,931 B2* | 10/2020 | Shuros | A61N 1/362 |
| 11,571,582 B2* | 2/2023 | Foster | A61N 1/3756 |
| 2007/0088418 A1* | 4/2007 | Jacobson | A61N 1/37217 607/116 |
| 2015/0230699 A1* | 8/2015 | Berul | A61B 1/05 600/104 |
| 2018/0256902 A1* | 9/2018 | Toy | A61B 90/39 |
| 2018/0264262 A1 | 9/2018 | Haasl et al. | |
| 2019/0134412 A1* | 5/2019 | Shuros | A61N 1/37205 |
| 2019/0192864 A1 | 6/2019 | Koop et al. | |
| 2020/0306522 A1 | 10/2020 | Chen et al. | |
| 2021/0046306 A1 | 2/2021 | Grubac et al. | |
| 2021/0059717 A1* | 3/2021 | Kerns | A61N 1/37512 |
| 2022/0257283 A1 | 8/2022 | Schmidt et al. | |

OTHER PUBLICATIONS

International Search Report and Written Opinion of International Application No. PCT/IB2022/058663 dated Dec. 7, 2022, 10 pp.

* cited by examiner

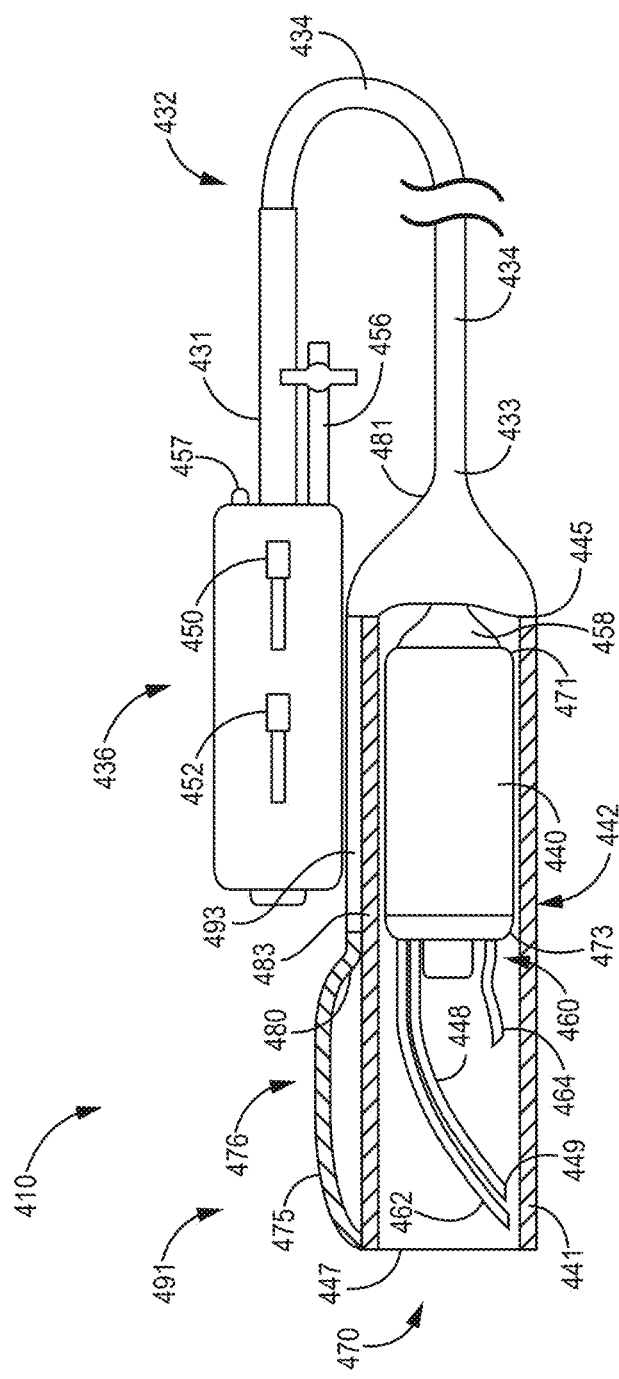

METHOD AND APPARATUS FOR IMPLANTING A MEDICAL DEVICE IN A CORONARY SINUS

This application claims the benefit of U.S. Provisional Patent Application Ser. No. 63/250,431, filed Sep. 30, 2021, the entire content of which is incorporated herein by reference.

BACKGROUND

The cardiac conduction system includes the sinus atrial (SA) node, the atrioventricular (AV) node, the bundle of His, bundle branches and Purkinje fibers. A heartbeat is initiated in the SA node, which may be described as the natural "pacemaker" of the heart. An electrical impulse arising from the SA node causes the atrial myocardium to contract. The electrical impulse, or electrical pulse or signal, is conducted to the ventricles via the AV node which inherently delays the conduction to allow the atria to stop contracting before the ventricles begin contracting thereby providing proper AV synchrony. The electrical impulse is conducted from the AV node to the ventricular myocardium via the bundle of His, bundle branches, and Purkinje fibers.

The leadless pacemaker, which is significantly smaller than a conventional pacemaker coupled to one or more transvenous leads, is a self-contained generator and electrode system configured to be implanted directly into the heart. The leadless pacemaker, which does not utilize leads extend from out of the heart of a patient, eliminates several complications associated with transvenous pacemakers and leads such as, for example, pocket infections, hematoma, lead dislodgment, and lead fracture. The leadless pacemaker also has cosmetic appeal because there is no chest incision or visible pacemaker pocket.

The leadless pacemaker includes one or more electrodes on its outer housing to deliver therapeutic electrical signals and/or sense intrinsic depolarizations of the heart. Intracardiac medical devices may provide cardiac therapy functionality, such as sensing and pacing, and may also be used to treat either atrial or ventricular arrhythmias or fibrillation.

The leadless pacemaker device may be implanted via a femoral vein transcatheter approach and requires no chest incision or subcutaneous generator pocket. The catheter system utilized to deploy the leadless pacemaker includes a distal end with a delivery cup housing the self-contained generator and electrode system, referred to herein as a pacing capsule. The delivery cup is maneuvered into the proper position, e.g., in the right atrium at or near the triangle of Koch (TOK) or the right ventricle, under fluoroscopic visualization or using a sonogram produced by an ultrasound imaging system.

SUMMARY

The distal tip of the delivery cup can be difficult to discern in a sonogram or other image used to monitor the position of the delivery cup during an implantation procedure, and in some cases the pacing capsule itself can cast a shadow that partially or even fully obscures the distal tip of the delivery cup in the sonogram image. In some cases, the difficulties in navigating the pacing capsule to the target tissue location in the TOK result in inaccurate placement of the distal end of the catheter. This inaccurate placement can cause the delivery cup on the distal end of the catheter to slide away from the target tissue in the TOK and enter the right ventricle, which can result in an insecure implantation of the pacing capsule, or even an unsuccessful implantation procedure.

Implantation of a leadless pacemaker device in the coronary sinus may provide an alternative to implantation in the TOK region for delivery of pacing to the left ventricle, the His Bundle, or other parts of the conduction system of the heart. In general, the present disclosure is directed to a system including a catheter for use in the delivery and implantation of a pacing capsule of an implantable medical device in the coronary sinus of a heart of a patient. A distal end of the catheter includes a delivery cup that releasably retains the pacing capsule. The delivery cup includes an inflatable balloon that, when inflated, urges the delivery cup against a target tissue location in the coronary sinus of the heart. While the delivery cup is temporarily fixed in position adjacent to the target tissue location by the inflated balloon, the pacing capsule of the leadless pacemaker can be deployed from the delivery cup. When deployed, an arrangement of tines on the pacing capsule pierce and engage the tissue of the coronary sinus to accurately implant the pacing capsule into an implant location in the coronary sinus of the patient.

In one example embodiment, the system of the present disclosure allows a practitioner to navigate the distal end of the catheter containing the delivery cup and the pacing capsule to a desired implant location in the coronary sinus with the balloon in an uninflated or partially inflated state. The balloon may then be inflated to apply a force against a first wall of the coronary sinus and temporarily fix the delivery cup into a deployment position against a second wall opposite the first wall. After the pacing capsule is deployed from the delivery cup and pierces the second wall to anchor the pacing capsule into the target tissue, the balloon may be deflated to facilitate removal of the catheter from the vasculature of the patient.

In many patients, in a sonogram image the coronary sinus is a more easily identifiable structure within the heart than the TOK, and cannulating the coronary sinus using a sonogram can be more reliable and reproducible for practitioners than locating the TOK. Once the desired implant location has been identified and the distal end of the catheter moved into position, the inflated balloon urges the delivery cup into a fixed deployment position in the coronary sinus, which can avoid dislocation or slippage of the delivery cup away from the TOK and into the right atrium or right ventricle. Temporarily anchoring the delivery cup in the coronary sinus with the inflated balloon makes implantation of the pacing capsule more reliable and reproducible, and places the implanted pacing capsule in a more effective position closer to the left ventricular tissue in the heart of the patient.

In one aspect, the present disclosure is directed to a system for delivery of a leadless pacemaker. The system includes a catheter with an elongate flexible tubular body with a proximal end and a distal end, wherein the distal end of the tubular body includes a delivery cup with an external surface having an inflatable compliant balloon; and a pacing capsule of the leadless pacemaker releasably retained in the delivery cup, wherein the pacing capsule includes an arrangement of tines configured to deploy and pierce a target tissue at a desired pacing capsule implant site in a coronary sinus of a patient. The balloon, when at least partially inflated, is configured to urge the delivery cup against the target tissue during deployment of the pacing capsule.

In another aspect, the present disclosure is directed to a method for implanting a leadless pacemaker in a target cardiac tissue. The method includes inserting into a vasculature of a patient a system for delivery of the leadless pacemaker, the system including: a catheter having an elongate flexible tubular body with a distal end having a delivery cup, and wherein an external surface of the delivery cup includes an inflatable compliant balloon; and a pacing capsule releasably retained in the delivery cup, wherein the pacing capsule includes an electrode and an arrangement of tines configured to affix the pacing capsule to the target cardiac tissue, wherein the target cardiac tissue is a wall of a coronary sinus; maneuvering the delivery cup in the vasculature of the patient to an implant location in the coronary sinus of the patient; at least partially inflating the balloon to urge the delivery cup against the target cardiac tissue and anchor the delivery cup at the implant location; and deploying the pacing capsule from the delivery cup such that the tines pierce the target tissue to embed the electrode in the target tissue and affix the pacing capsule in the target tissue at the implant location.

In another aspect, the present disclosure is directed to a method for implanting a leadless pacemaker in a target cardiac tissue in a coronary sinus of a patient. The method includes: inserting into a vasculature of a patient a system for delivery of the leadless pacemaker, the system including: a catheter having an elongate flexible tubular body with a distal end having a delivery cup, and wherein an external surface of the delivery cup includes an inflatable balloon; and a pacing capsule releasably retained in the delivery cup, wherein the pacing capsule includes an electrode and an arrangement of tines configured to affix the pacing capsule to the target cardiac tissue; maneuvering the delivery cup in the vasculature of the patient to an implant location in a first wall of the coronary sinus of the patient; inflating the balloon to urge the delivery cup against a second wall of the coronary sinus opposite a first wall and temporarily affix the delivery cup at the implant location; and deploying the pacing capsule from the delivery cup such that the tines pierce and embed in the first wall to implant the pacing capsule in the first wall, and the electrode embeds in the first wall.

The details of one or more examples are set forth in the accompanying drawings and the description below. Other features, objects, and advantages will be apparent from the description and drawings, and from the claims.

BRIEF DESCRIPTION OF DRAWINGS

FIG. 7 is a cross-sectional view of a leadless pacemaker implantation system including a delivery cup with a compliant balloon and configured to releasably retain the pacing capsule of FIGS. 2A-2D.

Like symbols in the drawings indicate like elements.

DETAILED DESCRIPTION

Figure 1:
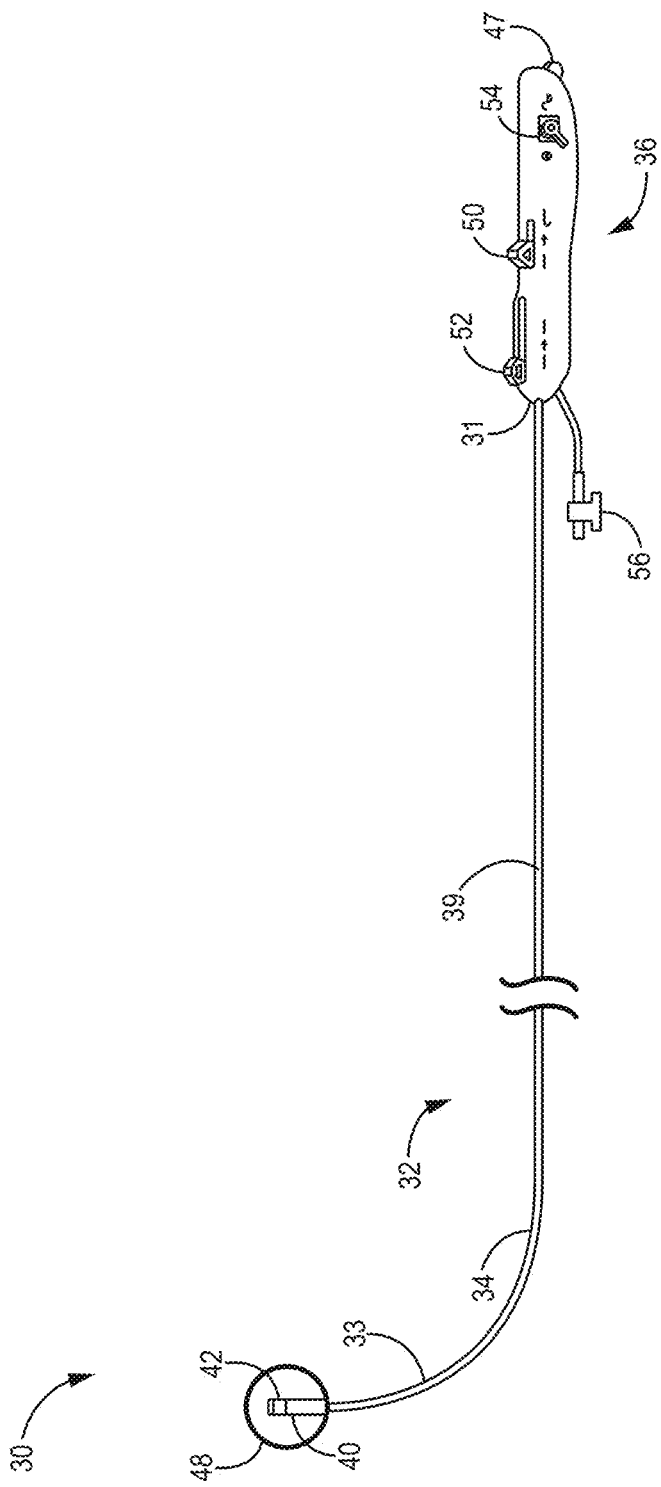
FIG. 1 is a schematic illustration of a system for guiding and implanting a leadless pacemaker into a target tissue.

FIG. 1 is a schematic illustration (which is not to scale) of a system 30 for guiding a pacing capsule of a leadless pacemaker to a desired implant location and implanting the pacing capsule into a target cardiac tissue. The system 30 includes an elongate tubular catheter 32 having a body 34 with a bore 39 that extends from a proximal end 31 to a distal end 33 thereof. In some examples, which are not intended to be limiting, the catheter body 34 has a length of about 75 centimeters (cm) to about 150 cm.

The proximal end 31 of the catheter body 34 is connected to a control handle 36 that can be used to deflect the catheter body 34 and deploy a pacing capsule 40. The pacing capsule 40 is releasably retained at the distal end 33 of the catheter body 34 in a delivery cup 42. Suitable leadless pacemaker pacing capsules 40 include, but are not limited to, those available from Medtronic, Inc., Minneapolis, MN, under the trade designation MICRA. The pacing capsule 40 includes a self-contained generator and electrode system that is implantable into cardiac tissue, and do not require leads or a subcutaneous pacemaker pocket like a transvenous pacemaker system.

The catheter body 34 may be placed in a suitable vein of a patient such as, for example, the femoral vein, and moved through the venous system to place a distal end 48 of the delivery cup 42 at a predetermined location in the heart. In some examples, the catheter body 34 may be deflected using an optional curve deflection control 50 on the handle 36. In some examples, the location of the catheter body 34 and a distal region 48 of the delivery cup 42 is monitored with an ultrasonic imaging system, and a sonogram image of the catheter body 34 and the delivery cup 42 is used to precisely position the delivery cup 42 in the heart. In some embodiments, during placement procedures a proximal portion of the pacing capsule 40 can optionally be tethered via a mechanical tether (not shown in FIG. 1) such as, for example, a tether pin 47.

Once the delivery cup 42 is positioned within the coronary sinus of the heart, the pacing capsule 40 is deployed from the delivery cup 42 via manipulation of the pacing capsule 40 or engagement of an optional deployment control 52 on the handle 36. The pacing capsule 40 can be implanted into the cardiac tissue using, for example, an arrangement of spring-loaded or self-expanding metal tines, a screw-in metal helix, and combinations thereof. After the pacing capsule 40 is implanted in the target tissue of the heart, a tether lock 54 on the handle 36 is released, and the catheter body 34 is withdrawn from the vascular system of the patient. The pacing capsule remains in position within the heart to provide suitable pacing therapy for the patient.

In some examples, the handle 36 may optionally include a fluid port 56, which can provide a fluid flush through the bore 39 of the catheter body 34 using a fluid such as, for example, water, saline, and the like.

In some examples (not shown in FIG. 1), the catheter 32 may optionally be placed within a rigid introducer including a tapered distal dilating tip to ease introduction of the catheter body 34 into the vasculature of the patient. For example, the dilating tip may be formed from an elastomeric material such as a silicone. In some examples, the introducer may optionally be coated with a lubricious hydrophilic coating.

Figure 2A:
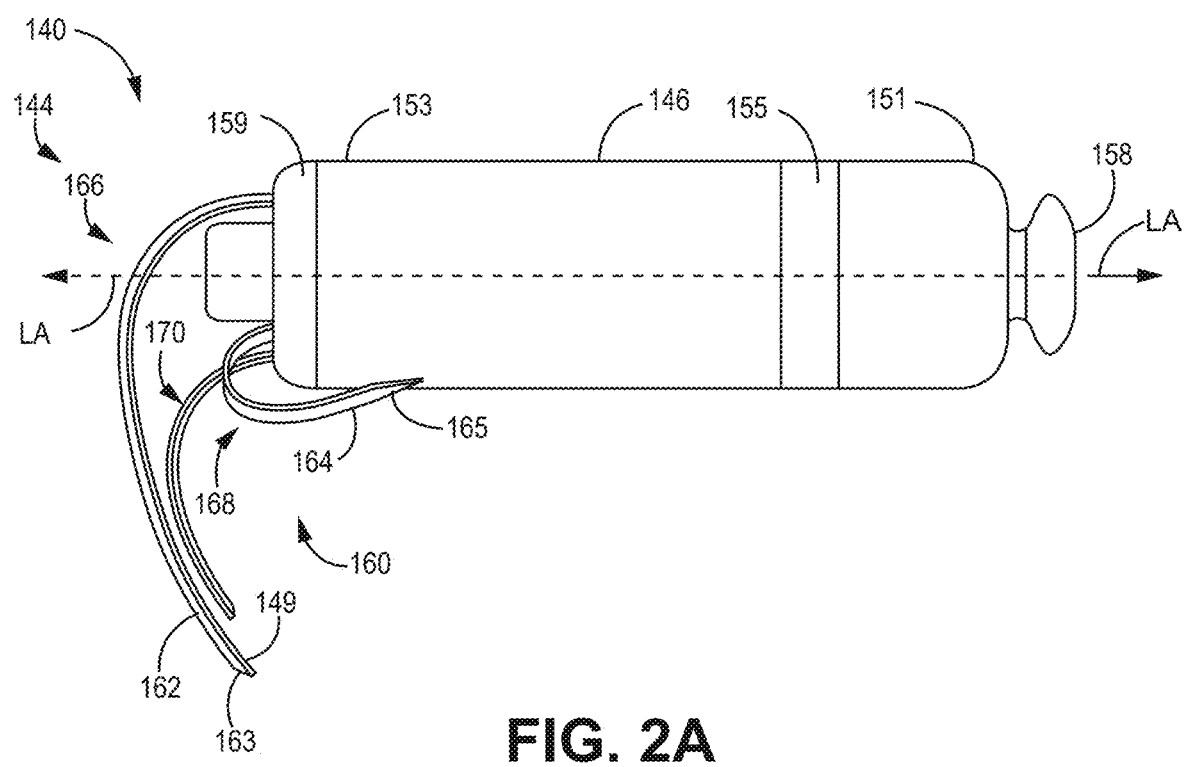
FIGS. 2A-2D are conceptual diagrams illustrating a pacing capsule for a leadless pacemaker.

FIG. 2A is a conceptual diagram illustrating a plan view of an example of a relatively compact pacing capsule 140 including a fixation component 144. The pacing capsule 140 of FIG. 2A includes a housing 146 extending along a longitudinal axis LA from a proximal end 151 to a distal end 153. The housing 146 may be formed from a biocompatible and biostable metal such as titanium, and in some examples, the housing 146 may be hermetically sealed. The housing 146 may include any suitable dimensions, and in some examples, has an outer diameter of between about 10 French (Fr) and about 30 Fr, such as about 20 Fr.

The pacing capsule 140 may contain electronic circuitry, including one or more of sensing circuitry (e.g., for sensing cardiac signals), therapy delivery circuitry (e.g., for generating cardiac pacing pulses), and processing circuitry for controlling the functionality of the pacing capsule 140, and may include one or more leadlets 148. The leadlet 148 may terminate in a distal electrode 149. For example, the leadlet 148 may include a conductor, such as an electrically conductive material, extending through a non-conductive jacket, such as polytetrafluoroethylene (PTFE) coating or polyether ether ketone (PEEK) tube, a portion of the conductor being exposed at electrode 149. The leadlet 148 may be used to control unipolar or bipolar pacing and sensing of different selected tissues. In some examples, the leadlet 148 may include an optional insulative layer, for example, medical grade polyurethane, parylene, or a silicone.

In some examples, the pacing capsule 140 can optionally include a second electrode (meant for surface atrial pacing, not shown in FIGS. 2A-2D) placed between the fixation tines 164. The second electrode can provide dual chamber pacing while the pacing capsule 140 lays against the tissue in the coronary sinus of the patient.

The electronic circuitry in the pacing capsule 140 may be configured to generate and deliver an electrical pulse therapy to tissue proximate leadlet 148 via first electrode 149, through the tissue to a return electrode 155. The leadlet 148 may be spaced apart from a distal end 153 of the housing 146, for example, being coupled to the sensing and therapy delivery circuitry by the conductor of a hermetic feedthrough assembly (not shown).

In some examples, the pacing capsule 140 includes an optional retrieval structure 158 fixedly attached to the proximal end 151 of the housing 146. The retrieval structure 158 may be configured for temporarily tethering the pacing capsule 140 to a delivery catheter or a retrieval catheter, or may be configured to couple to mechanical tether assemblies.

The fixation component 144 includes an arrangement of tines 160. In the embodiment of FIG. 2A, the fixation component 144 includes a base 159 affixed to the housing 146 of the pacing capsule 140, a penetrator tine 162, one or more optional fixation tines 164, and an optional support tines 170. However, as shown in more detail below, the fixation component 144 may include a wide variety of tine shapes, numbers of tines, and the like. Some examples of suitable tine arrangements, shapes and the like may be found in U.S. application Ser. No. 16/990,239, which is incorporated by reference herein in its entirety. The tines 160 may include one or more preset curved sections and one or more optional substantially straight sections. For example, the penetrator tine 162 may include preset curvature 166, and fixation tine 164 may include a preset curvature 168. In some examples, the tines 160 may define a ribbon shape configured to deform along a plane normal to longitudinal axis LA and resist twisting outside of that plane.

Figure 2B:
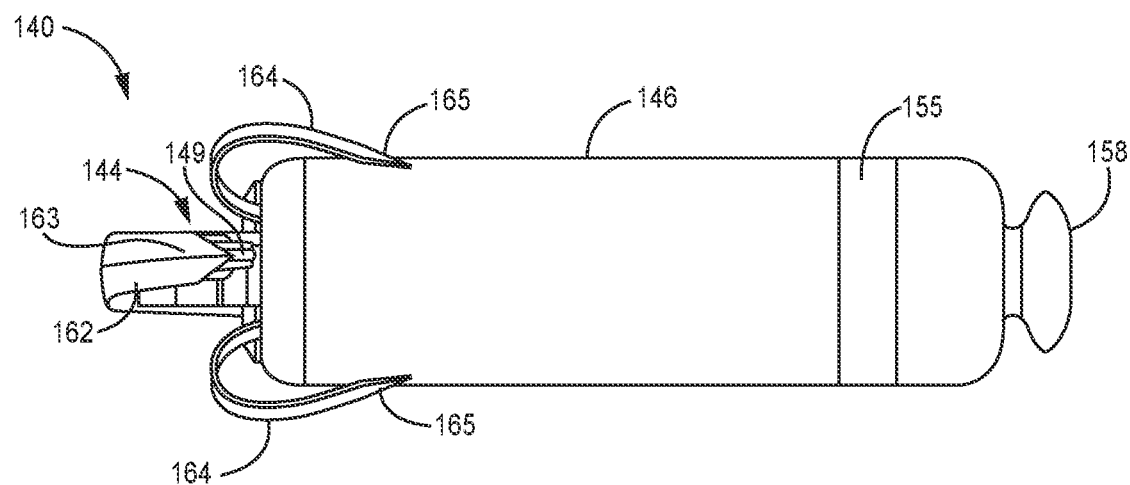
Figure 2C:
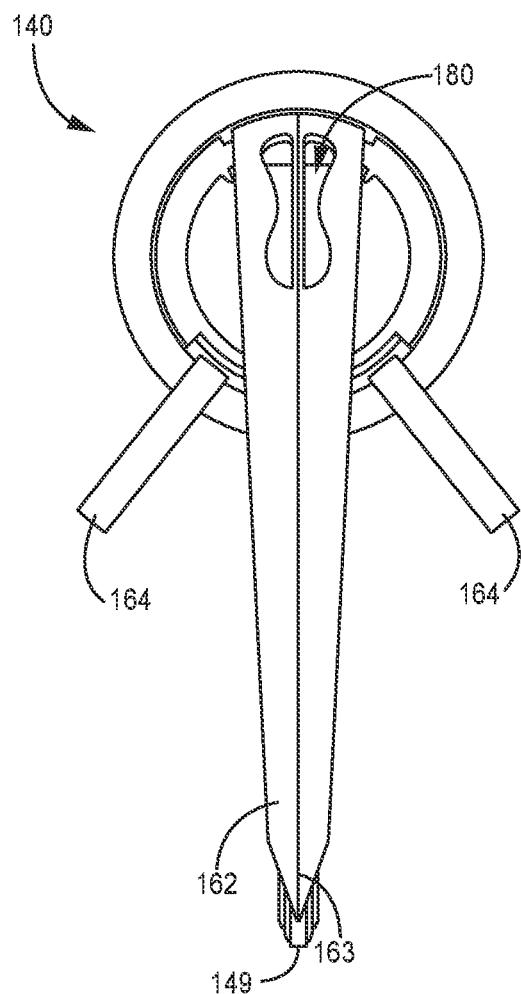
Figure 2D:
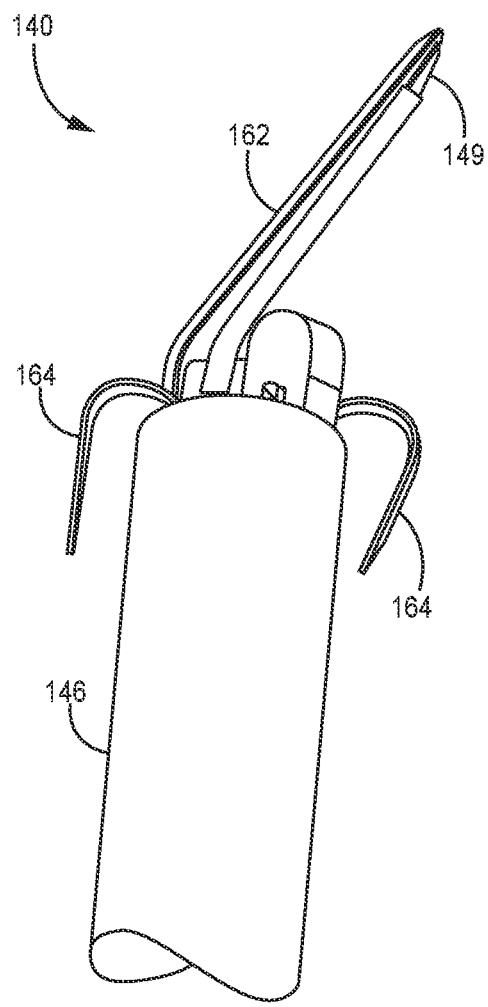

As further illustrated in FIGS. 2B-2D, the penetrating tine 162 is configured to guide the pacing capsule 140 to the target tissue area, while the fixation tine 164 supports the penetrating tine 162 as the electrode 149 penetrates the target tissue. The fixation tines 164 are biased to one side of the body 146 of the pacing capsule 140, which allows the pacing capsule 140 to implant when the pacing capsule 140 is parallel to the tissue (rather than requiring a substantially perpendicular approach). In some example embodiments, the fixation tines 164 can be anywhere from 5-90 degrees apart and may not be required if the penetrating tine 162 can properly prevent dislodgment of the pacing capsule 140 from a target tissue area. In some examples, the fixation tines 164 allow the pacing capsule 140 to implant substantially parallel to the target tissue. In various examples, to facilitate parallel implantation, the pacing capsule 140 can include no fixation tines 164, or up to 2 fixation tines 164 on a side of the pacing capsule 140, as well as an arrangement of penetrating tines 162 and optional support tines 170.

For example, the fixation tine 164 may be the same or substantially similar to tines described in U.S. Published Application No. 2020/0306522, which is incorporated by reference herein in its entirety. The fixation tines 164 may be configured to have a target deflection stiffness and a target deployment stiffness, which may include a measure of a resistance to force applied to the pacing capsule 140 in a proximal direction when fixation component 144 is engaged with tissue at a target implantation site. In some examples, the target deflection stiffness may be selected to enable the fixation tines 164 to deflect a predetermined amount to enable visualization of the fixation tines 164 under fluoroscopy. In some examples, the target deflection stiffness of the fixation tines 164 may be about 0.2 N to about 0.8 N, such as about 0.3 N to about 0.6 N. The deployment stiffness may include a measure of a force applied by the fixation tines 164 as the fixation tines 164 move from a deformed configuration to an undeformed configuration when the fixation component 144 is deployed from a distal opening of the delivery cup 42 (FIG. 1) such that the free distal ends 163, 165 of the tines 160 penetrates cardiac tissue. In some examples, the target deployment stiffness may be within a range from about 0.6 N to about 1.2 N.

The tines 160 may include any suitable elastically deformable biocompatible material. In some examples, the tines 160 may include a super-elastic material, such as, for example, a nickel titanium alloy. For example, the fixation component 144 may be cut from a medical grade nickel titanium alloy tubing that conforms to the chemical, physical, mechanical, and metallurgical requirements of the ASTM F2063 standard, and has a wall thickness of about 0.005 inch (0.127 mm). In this way, the tines 160 may be integrally formed with the base 159, and each tine of tines 160 may have a thickness of about 0.005 inch±0.001 inch (0.127 mm±0.0254 mm). In some examples, after cutting the tubing or otherwise forming fixation component 144, the tines 160 may be shaped into a preset configuration by bending and holding tines 160, while heat treating the construction according to methods known to those skilled in the art.

FIGS. 2B-2D illustrate different views of the pacing capsule 140. In some examples, as illustrated in FIG. 2C, the penetrator tine 162 may define an aperture 180. The aperture 180 may be configured to control a deployment stiffness or deflection stiffness of penetrator tine 162. For example, the aperture 180 may define a shear stress reduction region configured to reduce shear stress in penetrator tine 162 when bent, such as when bent into the deformed configuration or during a pull test or tug test.

Figure 3:
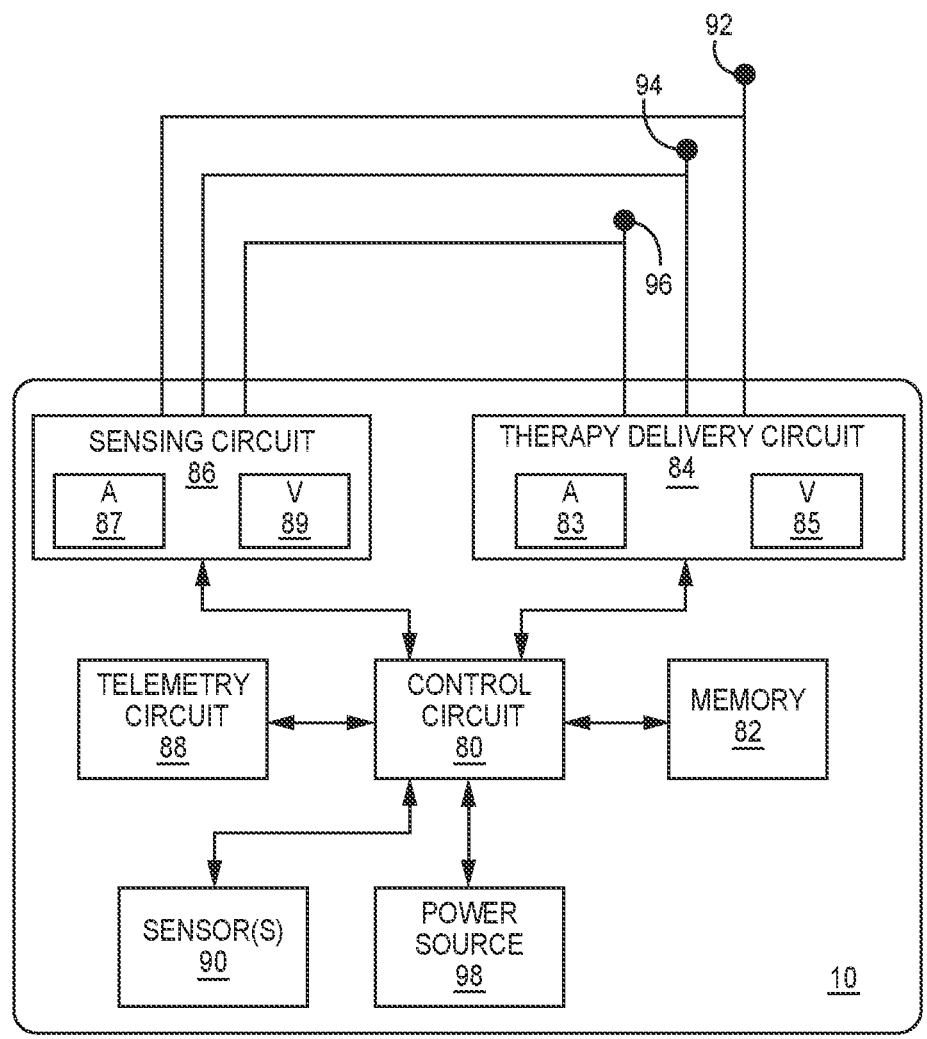
FIG. 3 is a conceptual circuit diagram of circuitry utilized in a housing of the pacing capsule of an embodiment of a leadless pacemaker of FIGS. 2A-2D.

FIG. 3 is a block diagram of circuitry that may be enclosed within the housing 146 (FIG. 2A) of the pacing capsule 140 to provide the functions of calibrating pacing therapy and/or delivering pacing therapy, using the device 10 according to one example. The electronic circuitry enclosed within the housing 146 may include software, firmware, and hardware that cooperatively monitor atrial and ventricular electrical cardiac signals, determine when a cardiac therapy is necessary, and/or deliver electrical pulses to the patient's heart according to programmed therapy mode and pulse control parameters. The electronic circuitry may include a control circuit 80 (e.g., including processing circuitry), a memory 82, a therapy delivery circuit 84, a sensing circuit 86, and/or a telemetry circuit 88. In some examples, the device 10 includes one or more sensors 90 for producing a signal that is correlated to a physiological function, state, or condition of the patient, such as a patient activity sensor, for use in determining a need for pacing therapy and/or controlling a pacing rate. For example, one sensor 90 may include an inertial measurement unit (e.g., accelerometer) to measure motion.

The power source 98 may provide power to the circuitry of the device 10 including each of the components 80, 82, 84, 86, 88, 90 as needed. The power source 98 may include one or more energy storage devices, such as one or more rechargeable or non-rechargeable batteries. The connections (not shown) between the power source 98 and each of the components 80, 82, 84, 86, 88, 90, may be understood from the general block diagram illustrated to one of ordinary skill in the art. For example, the power source 98 may be coupled to one or more charging circuits included in the therapy delivery circuit 84 for providing the power used to charge holding capacitors included in the therapy delivery circuit 84 that are discharged at appropriate times under the control of the control circuit 80 for delivering pacing pulses, e.g., according to a dual chamber pacing mode such as DDI(R). The power source 98 may also be coupled to components of the sensing circuit 86, such as sense amplifiers, analog-to-digital converters, switching circuitry, etc., sensors 90, the telemetry circuit 88, and the memory 82 to provide power to the various circuits.

The functional blocks shown represent functionality included in the device 10 and may include any discrete and/or integrated electronic circuit components that implement analog, and/or digital circuits capable of producing the functions attributed to the medical device 10 herein. The various components may include processing circuitry, such as an application specific integrated circuit (ASIC), an electronic circuit, a processor (shared, dedicated, or group), and memory that execute one or more software or firmware programs, a combinational logic circuit, state machine, or other suitable components or combinations of components that provide the described functionality. The particular form of software, hardware, and/or firmware employed to implement the functionality disclosed herein will be determined primarily by the particular system architecture employed in the medical device and by the particular detection and therapy delivery methodologies employed by the medical device.

The memory 82 may include any volatile, non-volatile, magnetic, or electrical non-transitory computer-readable storage media, such as random-access memory (RAM), read-only memory (ROM), non-volatile RAM (NVRAM), electrically-erasable programmable ROM (EEPROM), flash memory, or any other memory device. Furthermore, the memory 82 may include a non-transitory computer-readable media storing instructions that, when executed by one or more processing circuits, cause the control circuit 80 and/or other processing circuitry to calibrate pacing therapy and/or perform a single, dual, or triple-chamber calibrated pacing therapy (e.g., single or multiple chamber pacing), or other cardiac therapy functions (e.g., sensing or delivering therapy), attributed to the device 10. The non-transitory computer-readable media storing the instructions may include any of the media listed above.

The control circuit 80 may communicate, e.g., via a data bus, with the therapy delivery circuit 84 and the sensing circuit 86 for sensing cardiac electrical signals and controlling delivery of cardiac electrical stimulation therapies in response to sensed cardiac events, e.g., P-waves and R-waves, or the absence thereof. Electrodes such as, for example, a tip electrode 92, a distal housing-based electrode 94, and a proximal housing-based electrode 96 may be electrically coupled to the therapy delivery circuit 84 for delivering electrical stimulation pulses to the patient's heart and to the sensing circuit 86 and for sensing cardiac electrical signals.

The sensing circuit 86 may include an atrial (A) sensing channel 87 and a ventricular (V) sensing channel 89. The distal housing-based electrode 94 and the proximal housing-based electrode 96 may be coupled to the atrial sensing channel 87 for sensing atrial signals, e.g., P-waves attendant to the depolarization of the atrial myocardium. In examples that include two or more selectable distal housing-based electrodes, the sensing circuit 86 may include switching circuitry for selectively coupling one or more of the available distal housing-based electrodes to cardiac event detection circuitry included in the atrial sensing channel 87. Switching circuitry may include a switch array, switch matrix, multiplexer, or any other type of switching device suitable to selectively couple components of the sensing circuit 86 to selected electrodes. The tip electrode 92 and the proximal housing-based electrode 96 may be coupled to the ventricular sensing channel 89 for sensing ventricular signals, e.g., R-waves attendant to the depolarization of the ventricular myocardium.

Each of the atrial sensing channel 87 and the ventricular sensing channel 89 may include cardiac event detection circuitry for detecting P-waves and R-waves, respectively, from the cardiac electrical signals received by the respective sensing channels. The cardiac event detection circuitry included in each of the channels 87 and 89 may be configured to amplify, filter, digitize, and rectify the cardiac electrical signal received from the selected electrodes to improve the signal quality for detecting cardiac electrical events. The cardiac event detection circuitry within each channel 87 and 89 may include one or more sense amplifiers, filters, rectifiers, threshold detectors, comparators, analog-to-digital converters (ADCs), timers, or other analog or digital components. A cardiac event sensing threshold, e.g., a P-wave sensing threshold and an R-wave sensing threshold, may be automatically adjusted by each respective sensing channel 87 and 89 under the control of the control circuit 80, e.g., based on timing intervals and sensing threshold values determined by the control circuit 80, stored in the memory 82, and/or controlled by hardware, firmware, and/or software of the control circuit 80 and/or the sensing circuit 86.

Upon detecting a cardiac electrical event based on a sensing threshold crossing, the sensing circuit 86 may produce a sensed event signal that is passed to the control circuit 80. For example, the atrial sensing channel 87 may produce a P-wave sensed event signal in response to a P-wave sensing threshold crossing. The ventricular sensing channel 89 may produce an R-wave sensed event signal in response to an R-wave sensing threshold crossing. The sensed event signals may be used by the control circuit 80 for setting pacing escape interval timers that control the basic time intervals used for scheduling cardiac pacing pulses. A sensed event signal may trigger or inhibit a pacing pulse depending on the particular programmed pacing mode. For example, a P-wave sensed event signal received from the atrial sensing channel 87 may cause the control circuit 80 to inhibit a scheduled atrial pacing pulse and schedule a ventricular pacing pulse at a programmed atrioventricular (AV) pacing interval. If an R-wave is sensed before the AV pacing interval expires, the ventricular pacing pulse may be inhibited. If the AV pacing interval expires before the control circuit 80 receives an R-wave sensed event signal from the ventricular sensing channel 89, the control circuit 80 may use the therapy delivery circuit 84 to deliver the scheduled ventricular pacing pulse synchronized to the sensed P-wave.

The therapy delivery circuit 84 may include atrial pacing circuit 83 and ventricular pacing circuit 85. Each pacing circuit 83, 85 may include charging circuitry, one or more charge storage devices such as one or more low voltage holding capacitors, an output capacitor, and/or switching circuitry that controls when the holding capacitor(s) are charged and discharged across the output capacitor to deliver a pacing pulse to the pacing electrode vector coupled to respective pacing circuits 83, 85. The tip electrode 92 and the proximal housing-based electrode 96 may be coupled to the ventricular pacing circuit 85 as a bipolar cathode and anode pair for delivering ventricular pacing pulses, e.g., upon expiration of an AV or VV pacing interval set by the control circuit 80 for providing atrial-synchronized ventricular pacing and a basic lower ventricular pacing rate.

The atrial pacing circuit 83 may be coupled to the distal housing-based electrode 94 and the proximal housing-based electrode 96 to deliver atrial pacing pulses. The control circuit 80 may set one or more atrial pacing intervals according to a programmed lower pacing rate or a temporary lower rate set according to a rate-responsive sensor-indicated pacing rate. Atrial pacing circuit may be controlled to deliver an atrial pacing pulse if the atrial pacing interval expires before a P-wave sensed event signal is received from the atrial sensing channel 87. The control circuit 80 starts an AV pacing interval in response to a delivered atrial pacing pulse to provide synchronized multiple chamber pacing (e.g., dual- or triple-chamber pacing).

Charging of a holding capacitor of the atrial or ventricular pacing circuit 83, 85 to a programmed pacing voltage amplitude and discharging of the capacitor for a programmed pacing pulse width may be performed by the therapy delivery circuit 84 according to control signals received from the control circuit 80. For example, a pace timing circuit included in the control circuit 80 may include programmable digital counters set by a microprocessor of the control circuit 80 for controlling the basic pacing time intervals associated with various single-chamber or multiple-chamber pacing (e.g., dual- or triple-chamber pacing) modes. The microprocessor of the control circuit 80 may also set the amplitude, pulse width, polarity, or other characteristics of the cardiac pacing pulses, which may be based on programmed values stored in the memory 82.

The device 10 may optionally include other sensors 90 for sensing signals from the patient for use in determining a need for and/or controlling electrical stimulation therapies delivered by the therapy delivery circuit 84. In some examples, a sensor indicative of a need for increased cardiac output may include a patient activity sensor, such as an accelerometer. An increase in the metabolic demand of the patient due to increased activity as indicated by the patient activity sensor may be determined by the control circuit 80 for use in determining a sensor-indicated pacing rate.

Control parameters utilized by the control circuit 80 for sensing cardiac events and controlling pacing therapy delivery may be programmed into the memory 82 via the telemetry circuit 88, which may also be described as a communication interface. The telemetry circuit 88 includes a transceiver and antenna for communicating with an external device, such as a programmer or home monitor, using radio frequency communication or other communication protocols. The control circuit 80 may use the telemetry circuit 88 to receive downlink telemetry from and send uplink telemetry to the external device. In some cases, the telemetry circuit 88 may be used to transmit and receive communication signals to/from another medical device implanted in the patient.

Figure 4:
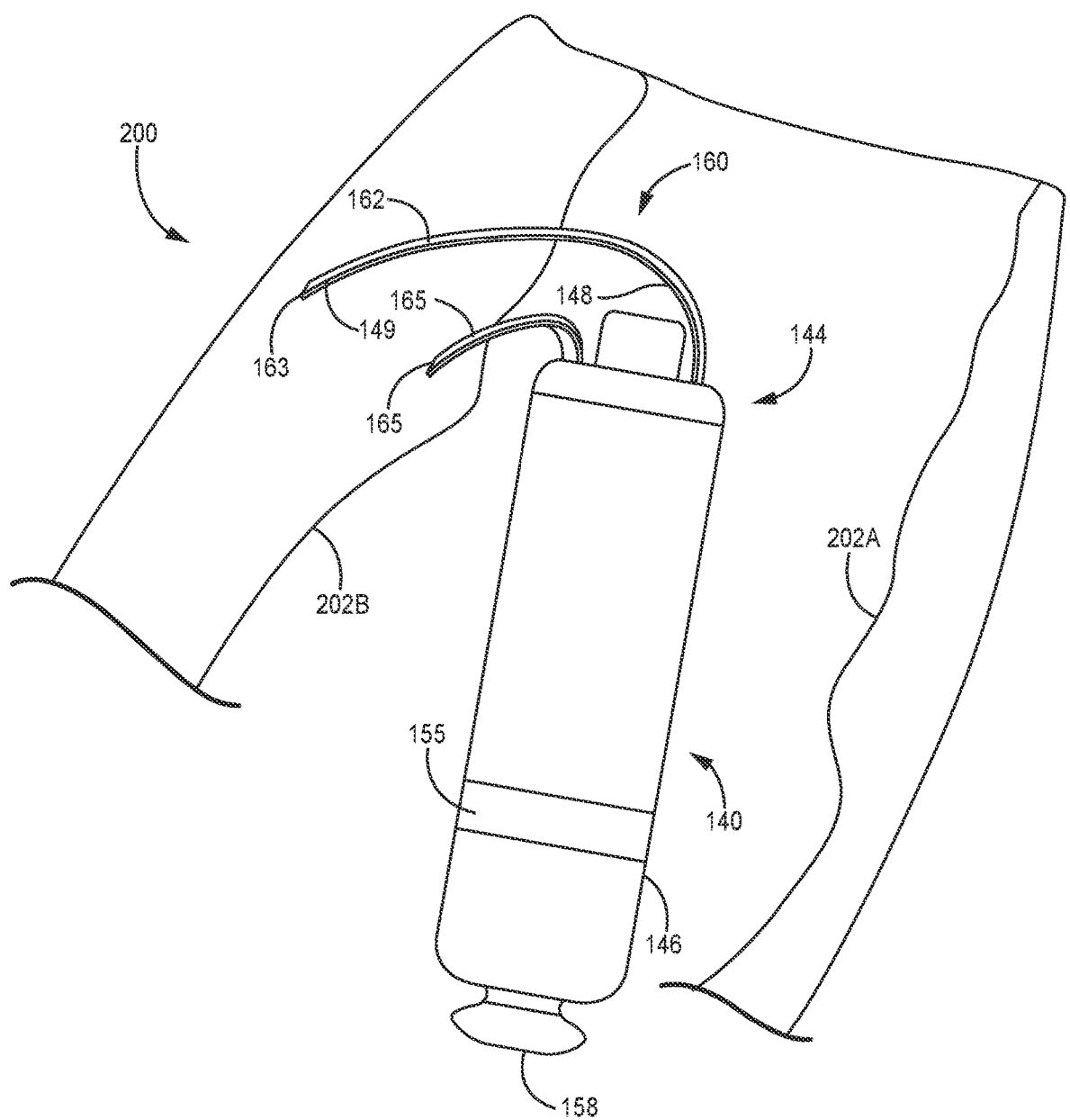
FIG. 4 is a schematic illustration of the pacing capsule of FIGS. 2A-2D affixed to a target tissue at a desired implant location in a coronary sinus of a heart of a patient.

FIG. 4 is a conceptual diagram illustrating the pacing capsule 140 implanted at a desired implant site 200 in the coronary sinus of a patient. The tines 160 define a deformable preset curvature configured to position the pacing capsule 140 at selected target tissue of the desired implant site 200, which is between opposed walls 202A, 202B of the coronary sinus. When deployed at target implant site 200, the tines 162, 164 have a deployment stiffness that enables the tines 162, 164 to penetrate selected target ventricular tissue at the desired implant site 200 such that the distal end 149 of the leadlets 148 is in the ventricular tissue of the wall 202B. For example, the pacing capsule 140 may be secured at the implant site 200 by the tines 162, 164 penetrating through the wall 202B of the coronary sinus. The tines 162, 164 are configured for spring-loaded release, upon deployment out through distal opening of the delivery cup 142 (FIG. 1) such that the respective free distal ends 163, 165 of the tines 162, 164 penetrate the venous wall 202B.

In the method of the present disclosure, the target implant site 200 includes a portion of the ventricular tissue of the walls 202A, 202B of the coronary sinus where the atrial endocardium can be reached. The coronary sinus is a large vein located in the atrioventricular groove (coronary sulcus) between the left ventricle and the right atrium of the heart. This coronary sinus collects deoxygenated blood from several cardiac veins located around the heart muscle. At its origin, the coronary sinus drains into the right atrium, and ends at its junction with the great cardiac vein. The orifice of the coronary sinus resides at an inferior border of the triangle of Koch (TOK). The apex of the TOK corresponds to the central fibrous body (CFB) of the heart where the His bundle penetrates, and the TOK is bordered posteriorly by a fibrous extension from the Eustachian valve referred to as the tendon of Todaro. The anterior border of the TOK is demarcated by the hinge (annulus) of the septal leaflet of the tricuspid valve. Since the coronary sinus is easily identifiable under sonogram and proximal the TOK, in some patients implanting the pacing capsule 140 within the tissue of the coronary sinus can provide more reproducible implantation while maintaining excellent pacing performance.

The coronary sinus is located in the posterior portion of the coronary sulcus on the diaphragmatic or posterior surface of the heart. The coronary sinus empties directly into the right atrium near the conjunction of the posterior interventricular sulcus and the coronary sulcus (crux cordis area), located between the inferior vena cava and tricuspid valve. This atrial ostium can be partially covered by a Thebesian valve, although the anatomy of this valve may in some cases be variable. The coronary sinus receives drainage from most epicardial ventricular veins, including the oblique vein of the left atrium (and other left and right atrial veins), the great cardiac vein, the posterior vein of the left ventricle, the left marginal vein, and the posterior interventricular vein. For example, the length of the coronary sinus in adults can vary from about 15 mm to about 65 mm.

Figure 5:
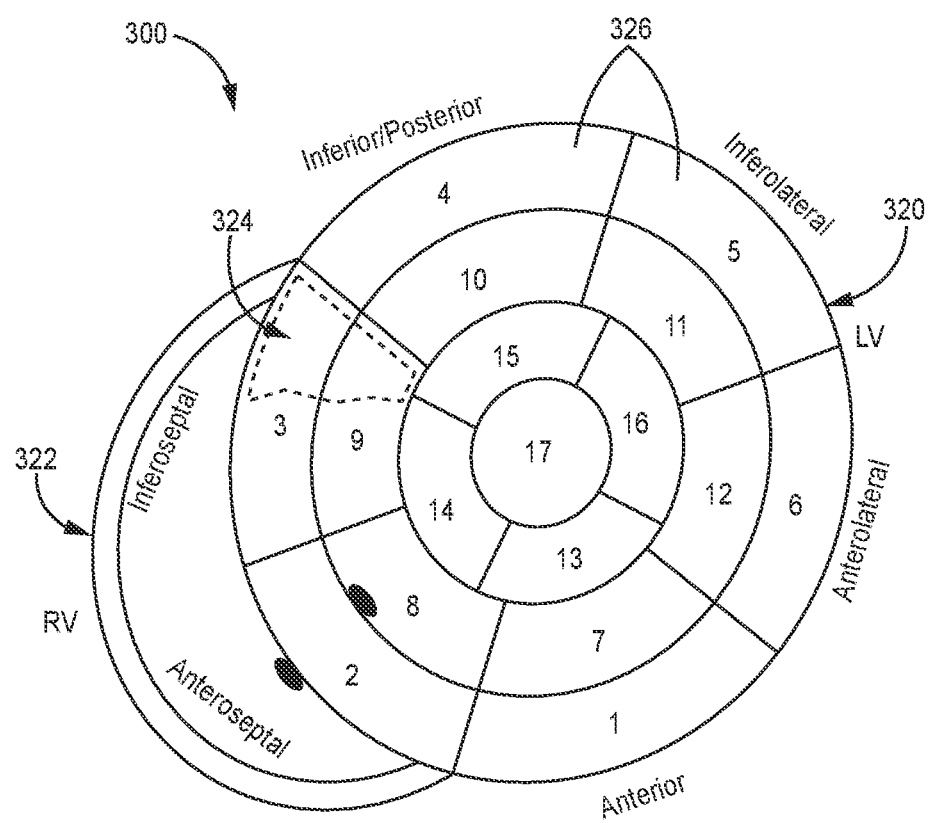
FIG. 5 is a conceptual diagram of a map of a heart of a patient showing implantation locations in the coronary sinus for use with, e.g., the illustrative systems and devices of the present disclosure.

FIG. 5 is a two-dimensional (2D) ventricular map 300 of a patient's heart (e.g., a top-down view) showing the left ventricle 320 in a standard 16 segment view and the right ventricle 322. The map 300 includes a plurality of areas 326 corresponding to different regions of a human heart. As illustrated, the areas 326 are numerically labeled 1-16 (e.g., which correspond to 16 segments of the left ventricle of a human heart). Areas 326 of the map 300 may include basal anterior area 1, basal anteroseptal area 2, basal inferoseptal area 3, basal inferior area 4, basal inferolateral area 5, basal anterolateral area 6, mid-anterior area 7, mid-anteroseptal area 8, mid-inferoseptal area 9, mid-inferior area 10, mid-inferolateral area 11, mid-anterolateral area 12, apical anterior area 13, apical septal area 14, apical inferior area 15, and apical lateral area 16. The inferoseptal and anteroseptal areas of the right ventricle 322 are also illustrated, as well as the right bundle branch (RBB) and left bundle branch (LBB).

Once implanted, leadlets 148 may be positioned in the target implant region 200 (FIG. 4). With reference to the map 300, possible implant locations for the distal end 149 of leadlets 148 include the basal inferoseptal area 3, the basal inferior area 4, the mid-inferoseptal area 9, and the mid-inferior area 10. With reference to map 300, the septal region includes one or more of the basal anteroseptal area 2, basal anteroseptal area 3, mid-anteroseptal area 8, mid-inferoseptal area 9, and the apical septal area 14. In some embodiments, leadlets 148 may be positioned in the area 324 in FIG. 5.

Figure 6:
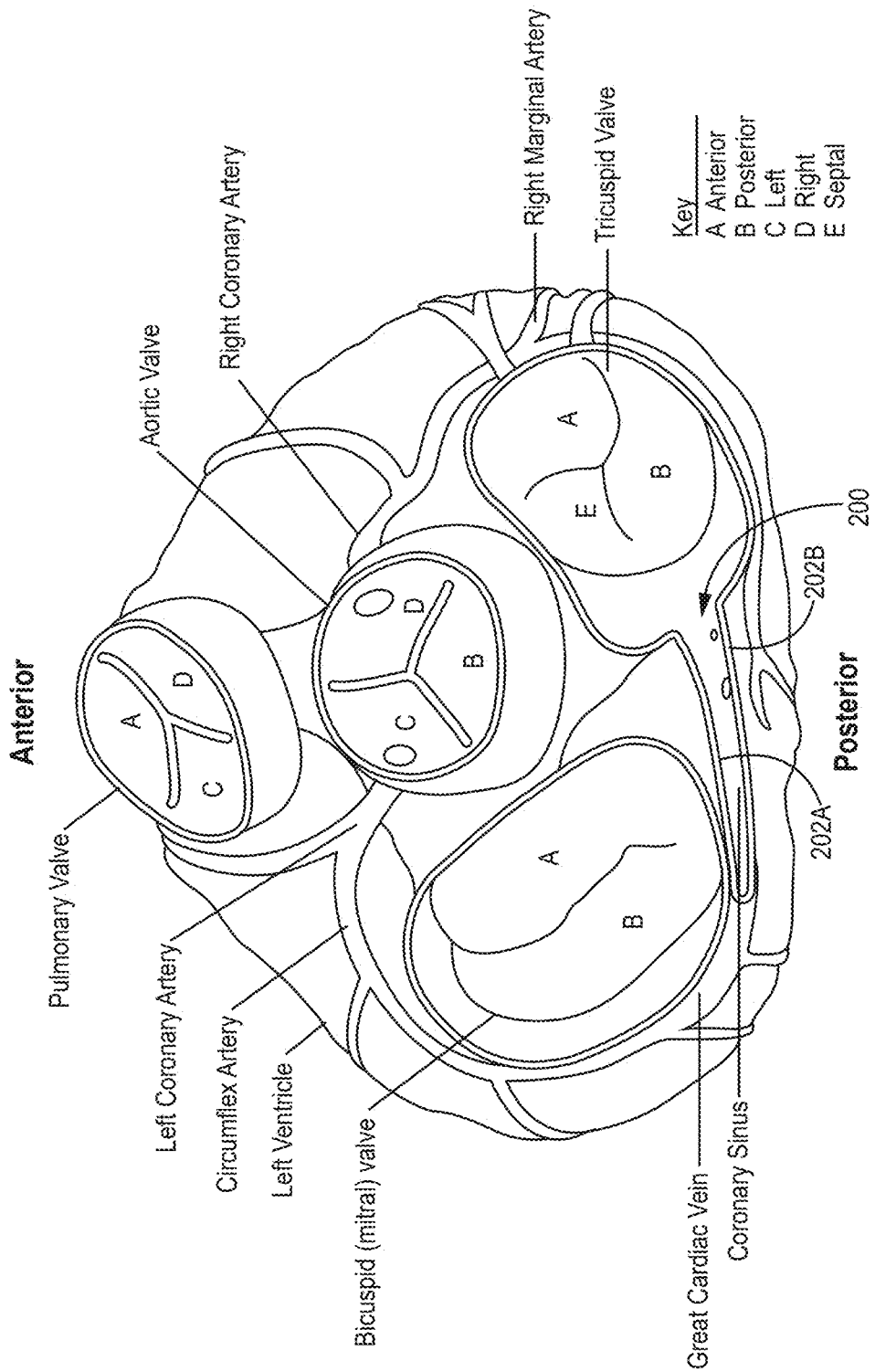
FIG. 6 is a conceptual diagram of a map of a heart of a patient showing implantation locations in the coronary sinus for use with, e.g., the illustrative systems and devices of the present disclosure.

FIG. 6 is a conceptual diagram of the heart showing the location of the walls 202A, 202B of the coronary sinus 200. The implant location for the pacing capsule 140 can be selected within ventricular tissue along the entire length of the coronary sinus, and the pacing capsule 140 can be implanted in the shown region of the coronary sinus/great cardiac vein with the distal tip 149 of leadlets 148 penetrating into the basal ventricular myocardium.

Referring now to FIG. 7, a system 410 includes a catheter delivery system 432 including a catheter body 434 with a distal region 491. The catheter body 434 can be made of any flexible material, including metals, polymeric materials, and the like. In some examples, the catheter body 434 is formed by extrusion of a polymeric material including, but not limited to, polyethylene (PE), nylon, polypropylene (PP), polyether block amide (PEBA), polybutylene terephthalate (PBT), and combinations thereof. In other examples, the catheter body 434 can be formed by processes including, but not limited to, molding, three-dimensional (3D) printing, additive manufacturing, and the like. In various examples, the catheter body 434 can be formed from a single layer of polymeric material, or multiple layers of the same or different polymeric materials.

In some examples, which are not intended to be limiting, the catheter body 434 has an outside diameter of about 0.100 inches (2.54 mm) to about 0.500 inches (12.7 mm), or about 0.200 inches (5.08 mm). In some examples, the catheter body 434 can optionally include a reinforcing or a catheter deflection material such as, for example, metal strands, ribbons, wires and the like (not shown in FIG. 7).

A proximal end 431 of the catheter body 434 is connected to a control handle 436 that can be used to deflect the catheter body 434 and deploy a leadless pacing capsule 440. The pacing capsule 440 is releasably retained in a delivery cup 442 positioned at a distal end 433 of the catheter body 434. As noted above with reference to FIG. 2, suitable leadless pacemaker pacing capsules 440 include those available from Medtronic, Inc., Minneapolis, MN, under the trade designation MICRA.

In some examples, the catheter body 434 may be deflected using an optional curve deflection control 452 on the handle 436. In some examples, during placement procedures the pacing capsule 440 remains tethered via an optional mechanical tether (not shown in FIG. 7) bound to a tether pin 457 in the control handle 436.

Once the delivery cup 442 is positioned and temporarily fixed at the proper location within the coronary sinus of the heart, the pacing capsule 440 is deployed from the delivery cup 442 using a deployment control 450 on the handle 436. The pacing capsule 440 is implanted into the cardiac tissue using a fixation component or implanting mechanism with an arrangement of the memory material metal tines 460. In the embodiment of FIG. 7, the tines 460 include a penetrator tine 462 and at least one fixation tine 464, which are depicted in a retracted position within the delivery cup 442.

The handle 436 further includes a fluid port 456, which can provide a fluid flush through the catheter body 434 using a fluid such as, for example, water, saline, and the like.

After the pacing capsule 440 is implanted in the tissue of the heart, a tether lock (not shown in FIG. 7) on the handle 436 is released and a tether (not shown in FIG. 7) is removed from a retrieval structure 458 on the pacing capsule 440, and the catheter body 434 is withdrawn from the vascular system of the patient.

In FIG. 7, the distal end 433 of the catheter body 434 includes the generally cylindrical and isodiametric delivery cup 442, which includes a wall 441 configured to securely retain the generally cylindrical pacing capsule 440 of the leadless pacemaker as the catheter body 434 is maneuvered through the vasculature of the patient. In various examples, the delivery cup 442 may be made from a polymeric material that may be the same or different from the polymeric material used to form the tubular body 434. In some examples, the delivery cup 442 may be made from a high impedance acoustic material, which in the present application refers to materials having an acoustic impedance higher than the acoustic impedance of a target tissue into which the pacing capsule 440 is to be implanted. In some examples, the delivery cup may be made from a low impedance acoustic material, which refers herein to materials having an acoustic impedance lower than the acoustic impedance of the target tissue.

In various examples, the delivery cup 442 may be a portion of the tubular body 434, may be a separate structure press-fit into the tubular body 434, or may be a separate structure bonded to the tubular body 434 by an adhesive, ultrasonic welding, overmolding, and the like. Like the catheter body 434, the delivery cup 442 may be formed by a wide variety of manufacturing processes including, but not limited to, extrusion, molding, 3D printing, additive manufacturing, and the like.

The delivery cup 442 includes a first end 445 that is integral with or connected to the distal end 433 of the tubular body 434 of the catheter 432. A distal second end 447 of the delivery cup 443 includes an aperture 470 through which the pacing capsule 440 is deployed.

The pacing capsule 440 includes a first proximal end 471 retained in the delivery cup 442 at the first end 445 thereof. A second distal end 447 of the delivery cup 442 is proximal the deployment aperture 470 and includes the metal tines 460. While retained in the delivery cup 442, the distal end 473 of the pacing capsule 440, as well as the tines 460, are substantially aligned near the distal end 447 of the delivery cup 442, and the tines 460 do not protrude from the aperture 470. The wall 441 of the delivery cup 442 maintains the orientation of the tines 460 until the pacing capsule 440 is deployed at a desired pacing capsule implantation site. When the pacing capsule 440 exits the delivery cup 442, the tines 460, which are retracted and maintained in position against the wall 441 of the delivery cup, spring out of the aperture 470 and extend laterally from a longitudinal axis of the delivery cup 442. Once deployed, at least one penetrator tine 462 and at least one fixation tine 464 are configured to pierce a target tissue and maintain the position and orientation of the pacing capsule 440 such that the distal end 449 of the electrode 448 remains embedded in the ventricular tissue of the coronary sinus of the patient.

The delivery cup 442 includes at least one balloon 476. In FIG. 7, the balloon 476 is shown in an inflated state, and in some examples, which are not intended to be limiting, has a conical or pear-like shape, but balloons with a wide variety of shapes can be used to fit into a selected region of coronary sinus tissue near a target implant site. The balloon 476 may be attached to an external surface 481 of the catheter 432, to an external surface 483 of the wall 441 of the delivery cup 442, or a combination thereof.

In some examples, which are not intended to be limiting, the balloon 476 is formed from a soft, flexible, compliant polymeric material such as, for example, polyethylene (PE)/ ethylene vinyl alcohol (EVA) blends, silicone, polyurethane, polyether block amide, thermoplastic elastomer, thermoplastic rubber and combinations thereof. However, in some examples, balloons formed from these materials may be made less compliant, or even relatively non-compliant. A more compliant balloon easily takes on the shape of the coronary sinus of a patient without applying excessive pressure to the vessel (to, for example, avoid dissection). The compliant balloon conforms to the shape necessary to occupy the coronary sinus and push the delivery cup 442 to a desired position to deploy the pacing capsule 440 in a desired orientation within the coronary sinus. In another example, a less compliant balloon with a more specific shape such as, for example, a funnel or a cork, may be more effective in plugging the coronary sinus of a patient during a procedure, may be useful to apply more pressure to the walls of the coronary sinus when the balloon is inflated.

In some embodiments, the balloon 476 is made of an echogenic material, and may be shaped to provide orientation feedback regarding the position of the distal end 447 of the delivery cup 442 on a sonogram image.

The balloon 476 includes a balloon wall 475 that may be formed from a single layer or multiple layers of polymeric materials and may optionally include reinforcing materials to enhance strength and burst resistance. In some examples, the balloon 476 may include at least one outer layer of an echogenic material.

In some examples, which are not intended to be limiting, the balloon 476 has a length of about 1 cm to about 10 cm. The balloon wall 475 can be attached to the external surfaces 481, 483 by any suitable technique including, for example, bonding, fusing, adhesives, and the like.

Figure 8A:
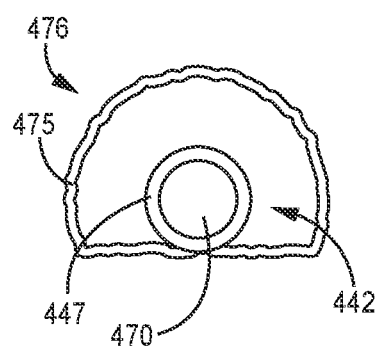
FIGS. 8A-8B are schematic illustrations of a distal end of a pacemaker implantation system.
Figure 8B:
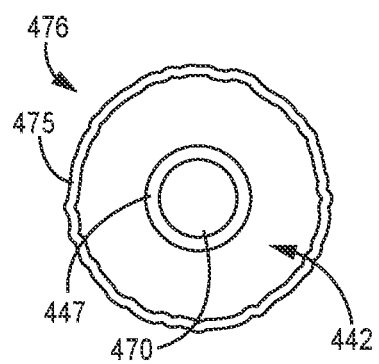

As shown schematically in FIG. 8A, in the embodiment of FIG. 7, the balloon 476 extends only a portion of the way around a circumference of the delivery cup 442. However, in other embodiments, as shown schematically in FIG. 8B, the balloon 476 may extend around the full circumference of the delivery cup 442.

In some embodiments (not shown in FIG. 7), the tubular body 434 or the delivery cup 442 may include multiple balloons 476 thereon, which may have the same shapes and sizes or different shapes and sizes, depending on the configuration of the tissue at an intended desired implant location, the force required to prevent dislodgement of the delivery cup 442 from a region of the coronary sinus during an implantation procedure, and the like.

The deployment of the balloon 476 can also provide a more echogenic shape to the delivery cup 442 without a required increase in the length of the delivery cup 442. The echogenic balloon is clearly visible and provides less obstructed sonogram images with improved clarity showing both the location of the distal tip 447 of the delivery cup 442 and the cardiac anatomy/tissue of a patient. The unobstructed sonogram images of the balloon provide improved confirmation of the location of the distal end 447 of the delivery cup 442 in the coronary sinus, as well as the implantation status of the pacing capsule 440 in the target cardiac tissue of the patient.

The thin, uninflated balloon 476 minimally increases the diameter of the device 410 during portions of the procedure where minimal diameter is important (for example, to provide improved venous access or to traverse smaller diameter veins).

Figure 9:
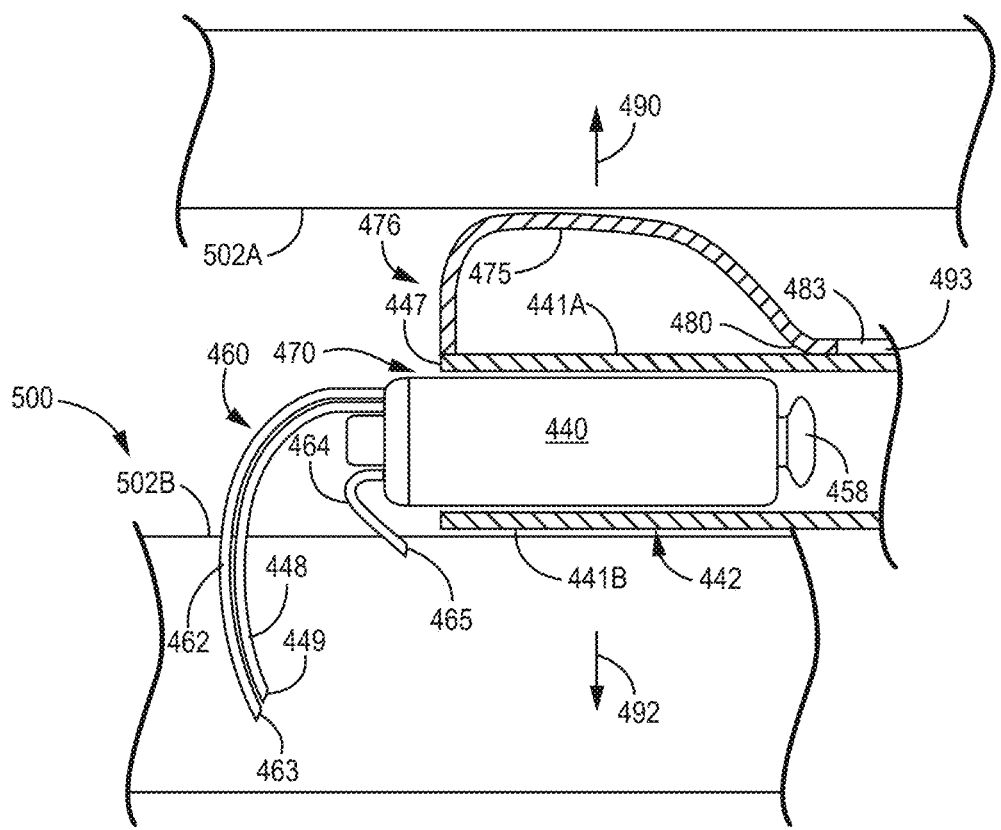
FIG. 9 is a schematic illustration of the delivery cup of the system of FIG. 7 during an implantation process at a target tissue in a desired implant location in a coronary sinus of a heart of a patient.

Referring now to the schematic depiction of FIG. 9, in operation, after the delivery cup 442 is positioned in a desired implant location 500 within the coronary sinus of the heart, a fluid is introduced into the balloon lumen 493 via, for example, a syringe, and exits a fluid egress port 480 in the balloon wall 475 to inflate and expand the balloon 476. In various examples, which are not intended to be limiting, the balloon 476 is inflated with an ultrasonically transparent fluid such as water or saline, a non-ultrasonically transparent fluid such as a radio-opaque contrast medium, or a mixture or combination thereof.

Once inflated, the wall 475 of the expanded compliant balloon 476 on a first side of the wall 441A of the delivery cup 442 conforms to a first wall portion 502A near a target implant location in the coronary sinus tissue 500. The expanded balloon wall 475 presses against the first wall portion 502A along a first direction 490, which urges a second side of the wall 441B of the delivery cup 442 along a generally opposed second direction 492 into position against an opposed second wall 502B at the target implant location. Once the delivery cup 442 is positioned and temporarily fixed in a desired position between the walls 502A, 502B at the target implant location, the pacing capsule 440 may be securely deployed from the aperture 470 at the distal end 447 of the delivery cup 442. Once the pacing capsule 440 emerges from the aperture 470, the spring-loaded tines 460 spring away and expand laterally from their deflected positions within the delivery cup 442 and move toward the wall 502B of the coronary sinus.

During and after deployment, the penetrator tine 462 has a deployment stiffness selected such that the tip 463 thereof penetrates the target tissue of the wall 502B generally along the direction 492. Following penetration, the tine 462 and the distal end 449 of the electrode 448 embeds in the target tissue within the second wall 502B. The fixation tine 465 assists in maintaining the position of the pacing capsule 442 against the wall 502B during and after the implantation procedure.

As shown schematically in FIG. 9, the tip 463 of the penetrator tine 462, as well as the tip 465 of the fixation tine 464, penetrate the target tissue of the coronary sinus wall 502B along the second direction 492, which is generally opposed to the first direction 490 along which force is applied against the coronary sinus wall 502A by the wall 475 of the compliant balloon 476. The constant force applied by the pressurized balloon 476 against the wall 502A urges the delivery cup 442 into position against the opposed wall 502B and thus assists the fixation tine 464 in maintaining the position of the pacing capsule 440 between the opposed walls 502A, 502B during the deployment procedure. The force applied by the inflated balloon 476 also resists movement of the delivery cup 442 and the pacing capsule 440 along the direction 490 toward the wall 502A as the tip 463 of the penetrator tine 462 pierces and lodges in the target tissue 502B. The force applied by the compliant balloon 476 can also prevent slippage of the delivery cup 442 or the pacing capsule 440 along the wall 502B during the deployment procedure. The force applied by the walls 475 of compliant balloon 476 thus enhances the accuracy and reliability of the procedure in which the pacing capsule 440 and the electrode 448 are implanted in the target tissue at the implant location in the coronary sinus tissue 502B.

Once the pacing capsule 440 is affixed in the implant location in the coronary sinus wall 502B and released from its tether, the balloon 476 may be at least partially deflated. The delivery cup 442 may then be withdrawn from the vasculature of the patient by removing the affixed catheter 432 (not shown in FIG. 9).

Figure 10:
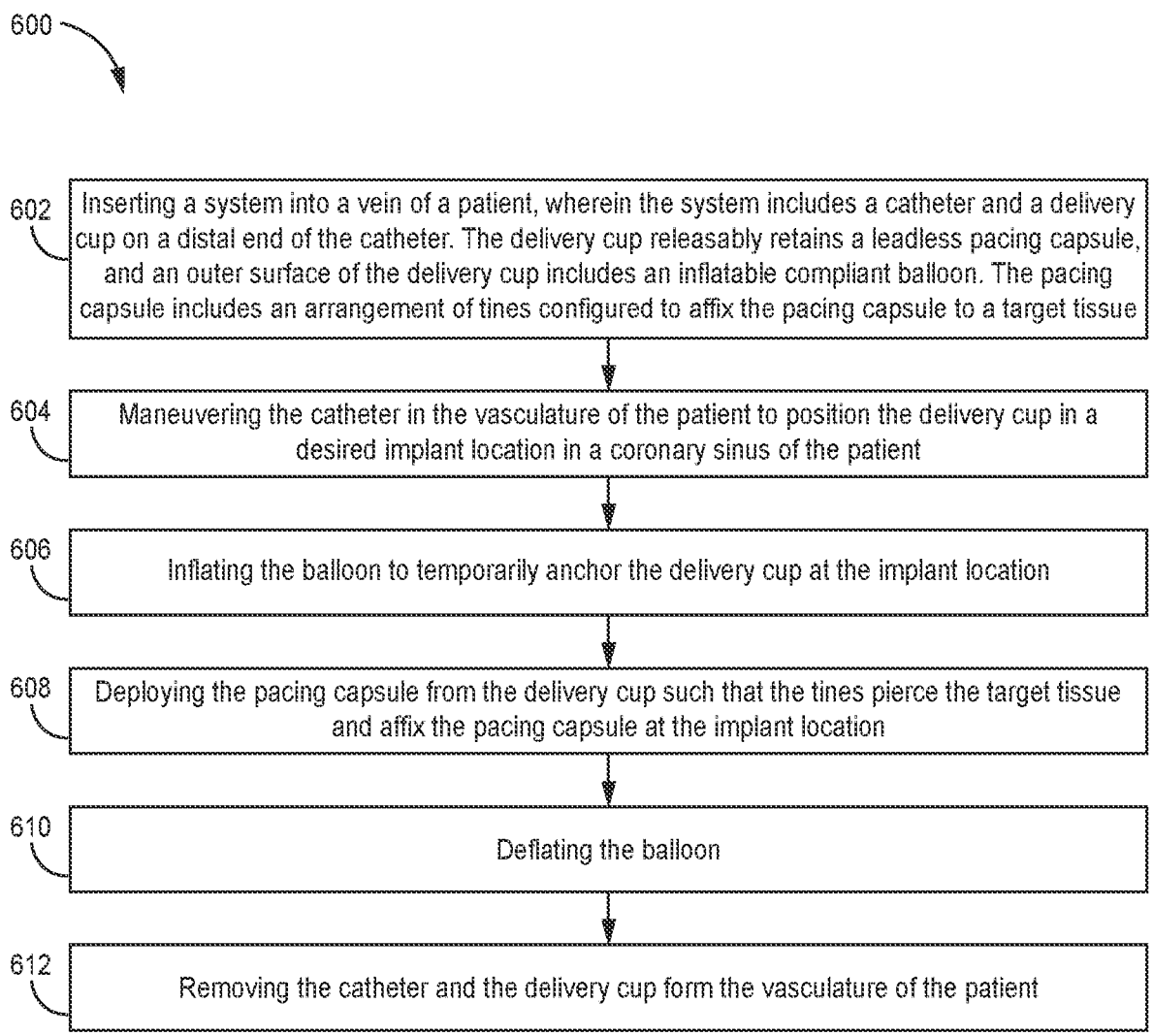
FIG. 10 is a flow chart of an illustrative example of a method for implanting a leadless pacemaker utilizing the devices of FIGS. 7-9.

In another aspect, the present disclosure is directed to a method of implanting an implantable medical device (IMD) such as, for example, a leadless pacemaker, in a coronary sinus of a heart of a patient. As shown in the flow chart of FIG. 10, the example method 600 includes inserting into an appropriate vein of a patient such as, for example, a femoral vein, a system for delivery of the leadless pacemaker (602). The system includes a pacing capsule and a catheter. The catheter includes an elongate flexible tubular body with a distal end having a delivery cup configured to releasably retain the pacing capsule. An outer surface of the delivery cup includes at least one balloon as described in FIGS. 8-9 above. The pacing capsule includes an arrangement of tines configured to pierce and affix the pacing capsule to a target tissue in the coronary sinus of the patient, and embed the distal tip of the electrode in the coronary sinus wall.

While typically performed under fluoroscopy, the example method optionally includes monitoring the location of the delivery cup with an ultrasonic imager to provide a sonogram. Any suitable ultrasonic imaging system may be used, and in some examples the imaging system includes an ultrasonic probe that moves along an external surface of the skin of the patient. In another example, an intracardiac echo (ICE) probe may be inserted into the femoral vein of the patient and maneuvered into position in the right atrium or right ventricle to image the anatomy of the patient. In various examples, which are not intended to be limiting, suitable probe apparatus include ultrasonic probes available from General Electric (GE), Philips, Siemens and the like. In various examples, which are provided by way of example and are not intended to be limiting, the transducers in the ultrasonic probe apparatus operate over a frequency range of about 1 MHz to about 60 MHz, or about 3 MHz to about 10 MHz for imaging procedures, and have a focal length of about 1 cm to about 4 cm, or about 2 cm to about 3 cm.

The example method 600 further includes maneuvering the catheter within the vasculature of the patient to position the delivery cup into an implant location in the coronary sinus of the patient (604). In some examples, the location of the delivery cup can be monitored in the sonogram.

The example method 600 further includes inflating the balloon to urge the delivery cup against the target tissue and temporarily anchor the delivery cup at the implant location (606).

After the delivery cup is anchored at the implant location by the balloon, the method 600 further includes deploying the pacing capsule from the delivery cup via the catheter 34 (FIG. 1) or an external tool such that at least some of the tines and the distal tip of the electrode pierce the target tissue and affix the pacing capsule at the implant location (608).

The example method 600 further includes at least partially deflating the balloon (610) and removing the catheter and the delivery cup from the vasculature of the patient (612).

The following examples are illustrative of the techniques described herein.

Example 1: A system for delivery of a leadless pacemaker, the system comprising: a catheter comprising an elongate flexible tubular body with a proximal end and a distal end, wherein the distal end of the tubular body comprises a delivery cup with an external surface comprising an inflatable compliant balloon; and a pacing capsule of the leadless pacemaker releasably retained in the delivery cup, wherein the pacing capsule comprises an arrangement of tines configured to deploy and pierce a target tissue at a desired pacing capsule implant site in a coronary sinus of a patient; and wherein the balloon, when at least partially inflated, is configured to urge the delivery cup against the target tissue during deployment of the pacing capsule.

Example 2: The system of claim 1, wherein the balloon resides on a first side of the delivery cup, and the tines on the pacing capsule are configured to deploy from the delivery cup toward a second side of the delivery cup opposite the first side thereof.

Example 3: The system of claim 1 or 2, wherein the arrangement of tines comprises at least one penetrator tine with a tip configured to pierce and penetrate the target tissue.

Example 4: The system of claim 3, wherein the arrangement of tines further comprises at least one fixation tine with a tip configured to pierce and penetrate the target tissue.

Example 5: The system of any one or more of claims 1-4, wherein the delivery cup comprises a fluid egress port fluidly connected to the balloon.

Example 6: The system of any one or more of claims 1-5, wherein the balloon comprises a polymeric material chosen from polyethylene (PE), ethylene vinyl alcohol (EVA), silicone, polyurethane, polyether block amide, and mixtures and combinations thereof.

Example 7: The system of any one or more of claims 1-6, wherein the balloon extends around a portion of a circumference of an external surface of the delivery cup, and wherein the portion of the circumference is less than the entire circumference.

Example 8: The system of any one or more of claims 1-6, wherein the balloon extends around a circumference of the external surface of the delivery cup.

Example 9: The system of any one or more of claims 1-8, wherein the delivery cup comprises a plurality of balloons.

Example 10: The system of any one or more of claims 1-9, wherein the balloon, when inflated with a fluid, has a conical shape.

Example 11: The system of claim 10, wherein the fluid is chosen from air, water, saline, and mixtures and combinations thereof.

Example 12: The system of any one or more of claims 1-11, wherein the balloon has a length of about 1 centimeters (cm) to about 10 cm, and an inflated diameter of about 2 cm to about 4 cm.

Example 13: The system of any one or more of claims 1-12, wherein the tubular body of the catheter comprises a polymeric material chosen from polyethylene (PE), nylon, silicone, polyurethane, polyether block amide, and combinations thereof.

Example 14: The system of any one or more of claims 1-13, wherein the tubular body comprises a metal reinforcing material.

Example 15: The system of any one or more of claims 1-14, wherein the tubular body further comprises a braid, a coil, or combinations thereof.

Example 16: The system of any one or more of claims 1-15, wherein the tubular body further comprises a pull wire.

Example 17: A method for implanting a leadless pacemaker in a target cardiac tissue, the method comprising: inserting into a vasculature of a patient a system for delivery of the leadless pacemaker, the system comprising: a catheter comprising an elongate flexible tubular body with a distal end having a delivery cup, and wherein an external surface of the delivery cup comprises an inflatable compliant balloon; and a pacing capsule releasably retained in the delivery cup, wherein the pacing capsule comprises an electrode and an arrangement of tines configured to affix the pacing capsule to the target cardiac tissue, wherein the target cardiac tissue is a wall of a coronary sinus; maneuvering the delivery cup in the vasculature of the patient to an implant location in the coronary sinus of the patient; at least partially inflating the balloon to urge the delivery cup against the target cardiac tissue and anchor the delivery cup at the implant location; and deploying the pacing capsule from the delivery cup such that the tines pierce the target tissue to embed the electrode in the target tissue and affix the pacing capsule in the target tissue at the implant location.

Example 18: The method of claim 17, further comprising: deflating the balloon; and removing the catheter and the delivery cup from the vasculature of the patient.

Example 19: The method of claim 17 or 18, further comprising: monitoring the location of the delivery cup with an ultrasonic imager to form a sonogram image; and maneuvering the delivery cup in the vasculature of the patient as shown in the sonogram image into the coronary sinus.

Example 20: The method of any one or more of claims 17-19, wherein the balloon overlies at least a portion of the external surface of the delivery cup.

Example 21: The method of any one or more of claim 17-20, wherein the balloon extends around a circumference of the external surface of the delivery cup.

Example 22: The method of claim 21, wherein the balloon extends around a portion of a circumference of the external surface of the delivery cup, and wherein the portion of the circumference is less than the entire circumference.

Example 23: The method of any one or more of claim 17-22, wherein the distal end of the catheter comprises a plurality of balloons.

Example 24: The method of claim any one or more of 17-23, wherein the balloon, when inflated with a fluid, has a conical shape.

Example 25: The method of any one or more of claims 17-24, wherein the balloon, when inflated, applies a force against a first wall of the coronary sinus, and the tines on the pacing capsule, deploy laterally from the delivery cup into a second wall of the coronary sinus opposite the first wall thereof.

Example 26: The method of claim 25, wherein the balloon urges the delivery cup against the second wall of the coronary sinus.

Example 27: The method of any one or more of claims 17-26, wherein the balloon is sufficiently compliant to avoid damage to a wall of the coronary sinus.

Example 28: A method for implanting a leadless pacemaker in a target cardiac tissue in a coronary sinus of a patient, the method comprising: inserting into a vasculature of a patient a system for delivery of the leadless pacemaker, the system comprising: a catheter comprising an elongate flexible tubular body with a distal end having a delivery cup, and wherein an external surface of the delivery cup comprises an inflatable balloon; and a pacing capsule releasably retained in the delivery cup, wherein the pacing capsule comprises an electrode and an arrangement of tines configured to affix the pacing capsule to the target cardiac tissue; maneuvering the delivery cup in the vasculature of the patient to an implant location in a first wall of the coronary sinus of the patient; inflating the balloon to urge the delivery cup against a second wall of the coronary sinus opposite a first wall and temporarily affix the delivery cup at the implant location; and deploying the pacing capsule from the delivery cup such that the tines pierce and embed in the first wall to implant the pacing capsule in the first wall, and the electrode embeds in the first wall.

Various examples have been described. These and other examples are within the scope of the following claims.

What is claimed is:

1. A system for delivery of a leadless pacemaker, the system comprising:
a catheter comprising an elongate flexible tubular body with a proximal end and a distal end, wherein the distal end of the tubular body comprises a delivery cup with an external surface comprising an expandable member; and
a pacing capsule of the leadless pacemaker releasably retained in the delivery cup, wherein the pacing capsule comprises an arrangement of tines comprising memory material configured to deploy and pierce a target tissue at a desired pacing capsule implant site in a coronary sinus of a patient; and
wherein the expandable member, when at least partially expanded, is configured to apply a force against a first wall of the coronary sinus to urge the delivery cup against the target tissue during deployment of the pacing capsule, and the tines on the pacing capsule are configured to deploy laterally from the delivery cup into a second wall of the coronary sinus opposite the first wall thereof when the delivery cup is urged against the target tissue.

2. The system of claim 1, wherein the expandable member resides on a first side of the delivery cup, and the tines on the pacing capsule are configured to deploy from the delivery cup toward a second side of the delivery cup opposite the first side thereof.

3. The system of claim 1, wherein the arrangement of tines comprises at least one penetrator tine with a tip configured to pierce and penetrate the target tissue.

4. The system of claim 3, wherein the arrangement of tines further comprises at least one fixation tine with a tip configured to pierce and penetrate the target tissue.

5. The system of claim 1, wherein the delivery cup comprises a fluid egress port fluidly connected to the expandable member.

6. The system of claim 1, wherein the expandable member comprises a balloon that comprises a polymeric material chosen from polyethylene (PE), ethylene vinyl alcohol (EVA), silicone, polyurethane, polyether block amide, and mixtures and combinations thereof.

7. The system of claim 1, wherein the expandable member extends around a portion of a circumference of an external surface of the delivery cup, and wherein the portion of the circumference is less than the entire circumference.

8. The system of claim 1, wherein the expandable member extends around a circumference of the external surface of the delivery cup.

9. The system of claim 1, wherein the delivery cup comprises a plurality of expandable members.

10. The system of claim 1, wherein the expandable member, when expanded, has a conical shape.

11. The system of claim 1, wherein the expandable member has a length of about 1 centimeters (cm) to about 10 cm, and an expanded diameter of about 2 cm to about 4 cm.

12. The system of claim 1, wherein the tubular body of the catheter comprises a polymeric material chosen from polyethylene (PE), nylon, silicone, polyurethane, polyether block amide, and combinations thereof.

13. The system of claim 1, wherein the tubular body comprises a metal reinforcing material.

14. The system of claim 1, wherein the tubular body further comprises a braid, a coil, or combinations thereof.

15. The system of claim 1, wherein the tubular body further comprises a pull wire.

16. A method for implanting a leadless pacemaker in a target cardiac tissue, the method comprising:
    inserting into a vasculature of a patient a system for delivery of the leadless pacemaker, the system comprising:
        a catheter comprising an elongate flexible tubular body with a distal end having a delivery cup, and wherein an external surface of the delivery cup comprises an expandable member; and
        a pacing capsule releasably retained in the delivery cup, wherein the pacing capsule comprises an electrode and an arrangement of tines configured to affix the pacing capsule to the target cardiac tissue, wherein the target cardiac tissue is a wall of a coronary sinus;
    maneuvering the delivery cup in the vasculature of the patient to an implant location in the coronary sinus of the patient;
    at least partially expanding the expandable member to urge the delivery cup against the target cardiac tissue and anchor the delivery cup at the implant location, wherein the expandable member, when expanded, applies a force against a first wall of the coronary sinus; and
    deploying the pacing capsule from the delivery cup so that the tines deploy laterally from the delivery cup and pierce into the target tissue to embed the electrode in the target tissue and affix the pacing capsule in the target tissue at the implant location, wherein the target tissue is a second wall of the coronary sinus opposite the first wall thereof.

17. The method of claim 16, further comprising:
    contracting the expandable member; and
    removing the catheter and the delivery cup from the vasculature of the patient.

18. The method of claim 16, further comprising:
    monitoring the location of the delivery cup with an ultrasonic imager to form a sonogram image; and
    maneuvering the delivery cup in the vasculature of the patient into the coronary sinus based on the sonogram image.

19. The method of claim 16, wherein the expandable member overlies at least a portion of the external surface of the delivery cup.

20. The method of claim 16, wherein the expandable member extends around a circumference of the external surface of the delivery cup.

21. The method of claim 20, wherein the expandable member extends around a portion of a circumference of the external surface of the delivery cup, and wherein the portion of the circumference is less than the entire circumference.

22. The method of claim 16, wherein the distal end of the catheter comprises a plurality of expandable members.

23. The method of claim 16, wherein the expandable member, when expanded, has a conical shape.

24. The method of claim 16, wherein the expandable member urges the delivery cup against the second wall of the coronary sinus.

25. The method of claim 16, wherein the expandable member is sufficiently compliant to avoid damage to a wall of the coronary sinus.

26. The method of claim 16, wherein the expandable member comprises an inflatable balloon.

27. A method for implanting a leadless pacemaker in a target cardiac tissue in a coronary sinus of a patient, the method comprising:
    inserting into a vasculature of a patient a system for delivery of the leadless pacemaker, the system comprising:
        a catheter comprising an elongate flexible tubular body with a distal end having a delivery cup, and wherein an external surface of the delivery cup comprises an expandable member; and
        a pacing capsule releasably retained in the delivery cup, wherein the pacing capsule comprises an electrode and an arrangement of tines configured to affix the pacing capsule to the target cardiac tissue;
    maneuvering the delivery cup in the vasculature of the patient to an implant location in a first wall of the coronary sinus of the patient;
    expanding the expandable member to urge the delivery cup against the first wall of the coronary sinus opposite a second wall and temporarily affix the delivery cup at the implant location, wherein the expandable member, when expanded, applies a force against the second wall of the coronary sinus; and
    deploying the pacing capsule from the delivery cup so that the tines deploy laterally from the delivery cup into the first wall to pierce and embed in the first wall to implant the pacing capsule in the first wall, and the electrode embeds in the first wall.

* * * * *